United States Patent
Oller Duque et al.

(10) Patent No.: US 11,426,427 B2
(45) Date of Patent: Aug. 30, 2022

(54) ISOTONIC CRYSTALLOID AQUEOUS SOLUTION

(71) Applicant: Lara Oller Duque, Madrid (ES)

(72) Inventors: Lara Oller Duque, Madrid (ES); Aryeh Shander, Demarest, NJ (US)

(73) Assignee: Lara Oller Duque, Madrid (ES)

( * ) Notice: Subject to any disclaimer, the term of this patent is extended or adjusted under 35 U.S.C. 154(b) by 721 days.

(21) Appl. No.: 16/320,706

(22) PCT Filed: Jul. 18, 2017

(86) PCT No.: PCT/EP2017/068141
§ 371 (c)(1),
(2) Date: Jan. 25, 2019

(87) PCT Pub. No.: WO2018/019663
PCT Pub. Date: Feb. 1, 2018

(65) Prior Publication Data
US 2021/0308179 A1    Oct. 7, 2021

(30) Foreign Application Priority Data
Jul. 26, 2016   (ES) .............................. ES201631021

(51) Int. Cl.
*A61K 33/20* (2006.01)
*A61K 33/24* (2019.01)
*A61K 33/242* (2019.01)
*A61K 33/241* (2019.01)
*A61P 9/10* (2006.01)
*A61P 7/08* (2006.01)
*A61K 9/08* (2006.01)
*A61K 33/00* (2006.01)
*A61K 33/04* (2006.01)
*A61K 33/06* (2006.01)

(52) U.S. Cl.
CPC .............. *A61K 33/20* (2013.01); *A61K 9/08* (2013.01); *A61K 33/00* (2013.01); *A61K 33/04* (2013.01); *A61K 33/06* (2013.01); *A61K 33/24* (2013.01); *A61K 33/241* (2019.01); *A61K 33/242* (2019.01); *A61P 7/08* (2018.01); *A61P 9/10* (2018.01)

(58) Field of Classification Search
CPC ....................................................... A61P 7/08
See application file for complete search history.

(56) References Cited

U.S. PATENT DOCUMENTS

| | | | | |
|---|---|---|---|---|
| 6,680,305 | B1* | 1/2004 | Segall | A61K 31/715 514/54 |
| 2004/0076687 | A1* | 4/2004 | Thompson | A61K 38/00 424/680 |
| 2006/0182815 | A1* | 8/2006 | Gladwin | A61K 33/00 424/718 |
| 2016/0067278 | A1* | 3/2016 | Bryland | A61K 33/00 |

OTHER PUBLICATIONS

Wisconsin Technical College, Nursing Fundamentals, Intravenous Solutions, downloaded in Aug. 2021 (Year: 2021).*
Wilhelm Jahnen-Dechent et al, Magnesium basics, Clin Kidney J (2012) 5[Suppl 1]: i3-i14 (Year: 2012).*
Lenntech, Composition of Seawater, Major ion composition of seawater, downloaded in Aug. 2021 (Year: 2021).*
Akiharu Hioki et al, Direct Determination Method of Nitrate Ions in Seawater by UV-Detection Ion-Chromatography with Hydrochloric Acid/Sodium Chloride Eluent, AIST Bulletin of Metrology vol. 7, No. 2, Dec. 2008 (Year: 2008).*
Nader Nezafati et al, Ion concentrations of human blood plasma and SBF, ResearchGate, Sep. 2012 (Year: 2012).*
Plasmalyte, Plasma-Lyte 148 (pH 7.4) solution for infusion—Summary of Product Characteristics, Baxter Healthcare Ltd, date of first authorization: May 8, 2009 (Year: 2009).*
Mychajlo Zakharchenko et al, The Effects of High Level Magnesium Dialysis/Substitution Fluid on Magnesium Homeostasis under Regional Citrate Anticoagulation in Critically Ill, PLOS One, DOI:10.1371/journal.pone.0158179 Jul. 8, 2016 (Year: 2016).*
Robert J Vissers et al, Iatrogenic Magnesium Overdose: Two Case Reports, The Journal of Emergency Medicine, vol. 14, No. 2, pp. 187-191, 1996 (Year: 1996).*
Andrea Bencini et al, Low Molecular Weight Compounds with Transition Metals as Free Radical Scavengers and Novel Therapeutic Agents, Cardiovascular & Hematological Agents in Medicinal Chemistry, 2010, 8, 128-146 (Year: 2010).*
International Search Report, PCT/EP2017/068141, 3 pages, dated Oct. 10, 2017.
Written Opinion dated Oct. 10, 2017 for Intl App No. PCT/EP2017/068141 (5 pages).

* cited by examiner

*Primary Examiner* — Mark V Stevens
*Assistant Examiner* — Alparslan Asan
(74) *Attorney, Agent, or Firm* — Kearney McWilliams & Davis, PLLC; John M. DeBoer

(57) ABSTRACT

The invention relates to an isotonic crystalloid aqueous solution of the type containing $Na^+$, $K^+$ and $Cl^-$, and to the use thereof as a vasodilator.

15 Claims, No Drawings ated administration of crystalloid solutions can reduce the
ISOTONIC CRYSTALLOID AQUEOUS SOLUTION The present invention relates to an isotonic crystalloid aqueous solution.

BACKGROUND OF THE INVENTION

Hemorrhagic shock is a very significant cause of death, and the administration of crystalloid solutions can reduce the severity and duration of shock.

A number of solutions which can be used in cases of blood loss as a blood substitute are known.

For example, the Dubick M. A. et al. document, "*Hypotensive resuscitation of casualties in the far forward combat environment: effects of select crystalloids and colloids on signal transduction mediators in a swine model of severe hemorrhage*," published in Selected topics in electronic and systems (2006); Vol. 42: 394-400, describes three solutions, one of said solutions being a colloid, Hextend, another one being HBOC (hemoglobin-based oxygen carriers), polyHeme, and another one being a crystalloid. These solutions do not contain nitrate ions, nitrite ions or chemical elements as metals and metalloids in their composition.

The Ozkän et al. document, "*Comparison of the effect of hypertonic saline and crystalloid infusions on haemodynamic parameters during haemorrhagic shock in dogs*" published in The Journal of International Medical Research, 2001, vol. 29:508-515, describes a comparative test on the efficacy of two crystalloid solutions in the recovery of dogs subjected to hemorrhagic shock. The compared crystalloids are, on one hand, a Ringer's lactate solution as standard treatment, and on the other hand a hypertonic saline solution consisting of 7.5% sodium chloride saline solution. None of the described solutions contains nitrate ions, nitrite ions or chemical elements as metals and metalloids It would be interesting to develop a new aqueous solution that yields better results than the already known solutions do.

DESCRIPTION OF THE INVENTION

The present invention describes an isotonic crystalloid aqueous solution containing nitrate ions or nitrite ions or a mixture thereof and metals and metalloids.

In the present description, "crystalloid aqueous solution" refers to a solution of ionic solutes used to replace fluids, primarily blood, which does not present oncotic pressure per se.

In the present invention, reference to isotonic solutions refers to solutions where the osmolarity in said solution is similar to that of extracellular fluid of the body, preferably blood, and does not change blood cell volume.

A first aspect of the invention relates to an isotonic crystalloid aqueous solution comprising $Na^+$ ions in a range comprised between 50 and 200 mmol/L, $K^+$ ions in a range comprised between 0.1 and 10 mmol/L, $Cl^-$ ions in a range comprised between 50 and 200 mmol/L, having nitrate ions or nitrite ions or a mixture thereof in a range comprised between 0.0001 mmol/l and 1 mmol/L and at least a chemistry element selected from: Li, Be, B, Al, Si, P, Sc, V, Cr, Mn, Fe, Co, Ni, Cu, Zn, As, Br, Rb, Sr, Y, Zr, Mo, Pd, Ag, Sn, Sb, I, Cs, Ba, Ce, Au, Tl, Pb, Bi, Th and U.

The solution of the present invention does not change the osmotic balance of cells.

An advantage of the presence of nitrate ions or nitrite ions or a mixture thereof, is that when the solution is perfused in a mammal, these ions have the potential to generate nitric oxide, a gas that generates vasodilatation. This leads to improved perfusion and oxygenation of tissues. This can be very useful, for example, in the recovery of subjects who are suffering hemorrhagic shock, which is associated with hypotension and hypovolemia which results in capillary collapse.

Another advantage of this invention is the presence of metals and metalloids in the crystalloid. These elements, when infused intravenously, have redox potential without deleterious effects on the organism. This function is very relevant because the chemical elements can behave as electron donors (reducing agent) that can be captured by oxidizing agents. This process describes a redox reaction (oxidation-reduction). Capillary collapse leads to cellular hypoxia and ischemia which results in a variety of cellular metabolic and ultrastructural changes. When oxygen is reintroduced during reperfusion, several enzyme systems will accelerate reactive oxygen species (ROS) production in postischemic tissues (xanthine oxidase, NADPH oxidase, the mitochondrial electron transport chain and uncoupled nitric oxide synthase), (Pathophysiology, clinical manifestations and prevention of Ischemia-reperfusion injury, Collard et al. Anesthesiology 2001, VOL 94, 1133-1138). ROS can behave as oxidizing agents and are highly reactive and unstable molecules. With reperfusion of ischemic tissue, an imbalance is created between the rate of generation of ROS and the tissue's ability to detoxify these reactive species, therefore, cellular damage will follow. (Reperfusion injury and reactive oxygen species: the evolution of a concept. D Neil Granger, Peter R. Kvietys. Redox Biology 6 (2015), 524-551). ROS are deleterious to cells, the microcirculation and the glycocalyx (the innermost endothelial layer) that is highly sensitive to them (The mechanisms and physiological relevance of glycocalyx degradation in hepatic ischemia/reperfusion injury. Rowan F. Van Golen et al. Antioxidants & Redox signaling. Volume 21, number 7, 2014). The ability of this crystalloid to neutralize reactive oxygen species would lead to preservation of glycocalyx, improvement of microcirculation and, therefore, attenuation of ischemia reperfusion injury. All this would lead to an improvement in survival in hemorrhagic shock.

The release of reactive oxygen species will take place after capillary recruitment and reperfusion, therefore, it is key that this isotonic crystalloid aqueous solution presents not only the ability to open collapsed capillaries thanks to the presence of nitrate and nitrite ions but the potential to neutralize reactive oxygen species. Thus, nitrates and nitrites have the potential to open up collapsed capillaries via nitrate-nitrite-nitric oxide pathway and the chemical elements that make up the solution will work together to neutralize reactive oxygen species through their redox potential. Explained it simple, nitrates and nitrites will "reconnect" capillaries collapsed to the systemic circulation and chemical elements will "sweep" the detritus generated during the time of "disconnection" from the systemic circulation. Capillaries preservation is fundamental for oxygen delivery to cells and oxygen uptake by cells, but so it is the integrity of the glycocalyx. A damaged glycocalyx will hinder the diffusion of oxygen from the vessel to the cells and also lead to a thickening of the interstitium, which may collapse the capillaries or, at least, make it difficult for blood cells to pass through them. Thus, oxygen delivery to cells depends on a correct microcirculation and this, in turn, requires a healthy glycocalyx. The solution of the present invention affects both key aspects; it is the synergy of both characteristics which explains the good results obtained in the experimental tests that we quote below.

Blood is the fluid conventionally used for treating patients who have experienced massive blood loss, but it does present many risks and is not always effective. The solution of the invention allows restoring microcirculation as a result of the presence of nitrates or nitrites, which may potentially be converted into nitric oxide (NO) after infusion into systemic circulation as a result of the nitrate-nitrite-nitric oxide pathway, as explained in a number of scientific papers, such as the Sruti Shiva document, "Nitrite: A physiological store of nitric oxide and modulator of mitochondrial function," published in Redox Biology 1 (2013) 40-44, or the Eddie Weitzberg et al. paper entitled "Nitrate-Nitrite-Nitric Oxide Pathway. Implications for Anesthesiology and Intensive Care" published in Anesthesiology 2010; 113:1460-75. Generating nitric oxide in a scenario of small vessel (capillary) disorder leads to capillaries restoration thus preserving perfusion and functional capillary density and, therefore, tissues oxygenation.

Therefore, the solution of the present invention has potential to generate nitric oxide, restore microcirculation without impairing macrocirculation or any other toxic effects.

A second aspect of the invention relates to the solution of the invention for use as a drug.

A third aspect of the invention relates to the solution of the invention for use as a vasodilator.

The solution described in the present invention is preferably useful in cases of hemorrhagic shock or acute normovolemic hemodilution.

Therefore, another aspect of the present invention is the solution of the invention for use in the treatment of hemorrhagic shock or in acute normovolemic hemodilution.

Another aspect of the invention is the solution of the invention for use as an intravenous fluid replacement.

The solution of the invention can also be useful in preventing injury caused by an episode of ischemia with later reperfusion (ischemia-reperfusion injury). Reference in the present invention to an episode of ischemia with later reperfusion refers to, for example, organ transplant, heart surgery-switching from extracorporeal circulation to physiological circulation, revascularization (blood flow restoration) of any tissue after an ischemic episode (infarction, stroke, etc.) by eliminating the STOP in circulation (angioplasty, thrombectomy, fibrinolysis, etc.) or hemorrhagic shock, in which the collapsed small vessels are reperfused after suitable treatment.

When a tissue has experienced a lack of oxygen supply (hypoxia-ischemia) due to the lack of perfusion, such as the heart during extracorporeal circulation, excess ROS are generated. Once hypoxic tissues are reperfused, ROS will be released causing damage to cells, the microcirculation and the glycocalyx (inner layer of the endothelium) as quoted before. This is one of the underlying processes of the phenomenon referred to as "ischemia-reperfusion injury".

It would therefore be useful to infuse the solution of the invention during reperfusion of the tissue that has experienced ischemia in order to attenuate ischemia-reperfusion injury.

Therefore, a final aspect of the invention is the solution of the invention for use in the prevention of ischemia-reperfusion injury.

DESCRIPTION OF A PREFERRED EMBODIMENT

In a preferred embodiment of the first aspect of the invention, the solution further comprises $Mg^{2+}$ in a range comprised between 1 and 20 mmol/L. In a second preferred embodiment of the first aspect of the invention, the solution further comprises $Mg^{2+}$ in a range comprised between 5 and 20 mmol/L.

In a third preferred embodiment of the first aspect of the invention, the solution comprises $Ca^{2+}$ ions in a range comprised between 1 and 20 mmol/L. In a fourth preferred embodiment of the first aspect of the invention, the solution further comprises $Ca^{2+}$ in a range comprised between 1 and 10 mmol/L.

In a fifth preferred embodiment of the first aspect of the invention, the nitrate ions or nitrite ions or mixtures thereof are comprised in a range between 0.0001 mmol/L and 1 mmol/L, preferably between 0.0001 mmol/L and 0.06 mmol/L, more preferably between 0.001 mmol/L and 0.06 mmol/L.

More preferably the first aspect of the invention, the solution further comprise $HCO_3^-$ in a range comprised between 0.1 mmol/l and 2 mmol/l.

More preferably the first aspect of the invention, the solution further comprise $SO_4^{2-}$ in a range comprised between 4 mmol/l and 8 mmol/l.

The pH of the solution is preferably between 5 and 10, more preferably between 6 and 9. In a particular embodiment, the pH of the solution at 22° C. is 6.9. In a particular embodiment, the solution of the invention has a solubility coefficient of 0.006 mg $O_2$/mmHg $pO_2$/dl at 36° C.

In a more preferred embodiment, the aqueous solution of the invention has chemistry elements selected from: Li, Be, B, Al, Si, P, Sc, V, Cr, Mn, Fe, Co, Ni, Cu, Zn, As, Br, Rb, Sr, Y, Zr, Mo, Pd, Ag, Sn, Sb, I, Cs, Ba, Ce, Au, Tl, Pb, Bi, Th and U, furthermore preferably Ho.

In a preferred embodiment, the aqueous solution of the invention has at least one chemistry element selected from: Li, Be, B, Al, Si, P, Sc, V, Cr, Mn, Fe, Co, Ni, Cu, Zn, As, Br, Rb, Sr, Y, Zr, Mo, Pd, Ag, Sn, Sb, I, Cs, Ba, Ce, Ho, Au, Tl, Pb, Bi, Th and U.

In a preferred embodiment, the aqueous solution of the invention has the following chemistry elements: Li, Be, B, Al, Si, P, Sc, V, Cr, Mn, Fe, Co, Ni, Cu, Zn, As, Br, Rb, Sr, Y, Zr, Mo, Pd, Ag, Sn, Sb, I, Cs, Ba, Ce, Ho, Au, Tl, Pb, Bi, Th and U.

In a particular embodiment, the aqueous solution has the following chemistry element at the following concentrations: $11.128 \cdot 10^{-3}$ mmol/L of Li, $0.0177 \cdot 10^{-3}$ mmol/L of Be, $144.73 \cdot 10^{-3}$ mmol/L of B, $0.82 \cdot 10^{-3}$ mmol/L of Al, $84.11 \cdot 10^{-3}$ mmol/L of Si, $0.39 \cdot 10^{-3}$ mmol/L of P, $8.0088 \cdot 10^{-6}$ mmol/L of Sc, $0.03866$ mmol/L of V, $8.46 \cdot 10^{-6}$ mmol/L of Cr, $0.37 \cdot 10^{-3}$ mmol/L of Mn, $0.31 \cdot 10^{-3}$ mmol/L of Fe, $0.009 \cdot 10^{-3}$ mmol/L of Co, $0.02 \cdot 10^{-3}$ mmol/L of Ni, $0.969 \cdot 10^{-3}$ mmol/L of Cu, $0.7576 \cdot 10^{-3}$ mmol/L of Zn, $0.0072 \cdot 10^{-3}$ mmol/L of As, $348.699 \cdot 10^{-3}$ mmol/L of Br, $0.459 \cdot 10^{-3}$ mmol/L of Rb, $29.63 \cdot 10^{-3}$ mmol/L of Sr, $0.00247 \cdot 10^{-3}$ mmol/L of Y, $0.0003288 \cdot 10^{-3}$ mmol/L of Zr, $0.0503 \cdot 10^{-3}$ mmol/L of Mo, $0.09 \cdot 10^{-6}$ mmol/L of Pd, $0.00129 \cdot 10^{-3}$ mmol/L of Ag, $0.00193 \cdot 10^{-3}$ mmol/L of Sn, $0.000082 \cdot 10^{-3}$ mmol/L of Sb, $0.58 \cdot 10^{-3}$ mmol/L of I, $0.0012 \cdot 10^{-3}$ mmol/L of Cs, $0.1054 \cdot 10^{-3}$ mmol/L of Ba, $0.00014 \cdot 10^{-3}$ mmol/L of Ce, $0.0040 \cdot 10^{-3}$ mmol/L of Au, $0.00102 \cdot 10^{-3}$ mmol/L of Tl, $0.022 \cdot 10^{-3}$ mmol/L of Pb, $0.01119 \cdot 10^{-3}$ mmol/L of Bi, $0.01267 \cdot 10^{-3}$ mmol/L of Th, $0.0047 \cdot 10^{-3}$ mmol/L of U, 170 mmol/L of Na, 17.17 mmol/L of Mg, 4.5 mmol/L of S, 4.6 mmol/L of K, 3.99 mmol/L of Ca and $0.000060 \cdot 10^{-3}$ of Ho.

Preferably the chemistry elements are: Li, Fe, Cu, Al, Mn, Zn, Sr, Sn, Pb, Br, S and P. More preferably the chemistry elements are: Li, Fe, Cu, Al, Mn, Zn, Sr, Sn and Pb.

Examples

The solution of the invention, Plasmalyte and whole blood (less than 20 days in storage), were used in the examples. The compositions of the solutions used are shown below.

Table 1 shows the composition of the solution of the invention used in tests.

|      | mmol/L   |
| ---- | -------- |
| $Na^+$     | 128.51   |
| $K^+$      | 2.7      |
| $Mg^{2+}$  | 12.32    |
| $Ca^{2+}$  | 3.082    |
| $Cl^-$     | 164      |
| $SO_4^{-2}$ | 6.47    |
| $HCO_3^-$  | 0.836    |
| $NO_3^-$   | <0.0484  |

Also the composition contains chemical elements such as: $11.128 \cdot 10^{-3}$ mmol/L of Li, $0.0177 \cdot 10^{-3}$ mmol/L of Be, $144.73 \cdot 10^{-3}$ mmol/L of B, $0.82 \cdot 10^{-3}$ mmol/L of Al, $84.11 \cdot 10^{-3}$ mmol/L of Si, $0.39 \cdot 10^{-3}$ mmol/L of P, $8.0088 \cdot 10^{-6}$ mmol/L of Sc, $0.03866$ mmol/L of V, $8.46 \cdot 10^{-6}$ mmol/L of Cr, $0.37 \cdot 10^{-3}$ mmol/L of Mn, $0.31 \cdot 10^{-3}$ mmol/L of Fe, $0.009 \cdot 10^{-3}$ mmol/L of Co, $0.02 \cdot 10^{-3}$ mmol/L of Ni, $0.969 \cdot 10^{-3}$ mmol/L of Cu, $0.7576 \cdot 10^{-3}$ mmol/L of Zn, $0.0072 \cdot 10^{-3}$ mmol/L of As, $348.699 \cdot 10^{-3}$ mmol/L of Br, $0.459 \cdot 10^{-3}$ mmol/L of Rb, $29.63 \cdot 10^{-3}$ mmol/L of Sr, $0.00247 \cdot 10^{-3}$ mmol/L of Y, $0.0003288 \cdot 10^{-3}$ mmol/L of Zr, $0.0503 \cdot 10^{-3}$ mmol/L of Mo, $0.09 \cdot 10^{-6}$ mmol/L of Pd, $0.00129 \cdot 10^{-3}$ mmol/L of Ag, $0.00193 \cdot 10^{-3}$ mmol/L of Sn, $0.000082 \cdot 10^{-3}$ mmol/L of Sb, $0.58 \cdot 10^{-3}$ mmol/L of I, $0.0012 \cdot 10^{-3}$ mmol/L of Cs, $0.1054 \cdot 10^{-3}$ mmol/L of Ba, $0.00014 \cdot 10^{-3}$ mmol/L of Ce, $0.0040 \cdot 10^{-3}$ mmol/L of Au, $0.00102 \cdot 10^{-3}$ mmol/L of Tl, $0.022 \cdot 10^{-3}$ mmol/L of Pb, $0.01119 \cdot 10^{-3}$ mmol/L of Bi, $0.01267 \cdot 10^{-3}$ mmol/L of Th, $0.0047 \cdot 10^{-3}$ mmol/L of U.

Table 2 shows the composition of the Plasmalyte solution used in the examples (data taken from Lira et al. Ann Intensive Care, 2014).

|            | mmol/L |
| ---------- | ------ |
| $Na^+$     | 140    |
| $K^+$      | 5      |
| $Mg^{2+}$  | 1.5    |
| $Cl^-$     | 98     |
| Acetate    | 27     |
| Gluconate  | 23     |
| Osmolarity | 294    |

The examples were carried out with pigs. All the animals are from the same crossbreed, all females and in a specific weight range. The protocol consists of draining between 40-60% of the blood volume estimated according to calculations (blood volume is 7% of the weight on average) to attain a lactic acid level greater than 5 mmol/L, which is correlated with a tissue oxygen debt of 75.2 mL/kg or higher according to Rixen et al. in their paper "A pig hemorrhagic shock model: oxygen debt and metabolic acidemia as indicators of severity". Given that the circulating blood volume of each animal ranges from 55 ml/kg to 74 ml/kg and the drained volume is not such a determining factor as it is the speed at which it is drawn and the tolerance of the animal to hypoxia, the objective that was established was to attain the degree of tissue oxygen debt indicated above. Then withdrawn blood volume was replaced with the solution of the invention (the drained blood volume was infused three times (3:1 ratio)), and lactic acid washing was measured during the minutes after replacement (T0=right after replacement, T15=15 minutes after replacement, T30=30 minutes after replacement, T1 h=one hour after replacement, T2 h=two hours after replacement) and intestinal microcirculation was analyzed with a microscan, paying particular attention to the proportion of perfused small vessels expressed as a percentage (small PPV: proportion of perfused small vessels expressed as a %). The animals were observed for 72 h after hemorrhagic shock in a barnyard having free access to water and food.

A drop in PPV was observed during the shock, and a PPV of 100% was observed in all the measured areas 60 minutes after replacement, demonstrating the capacity of the solution of the invention to open up those small vessels that collapsed during hemorrhagic shock and to do so homogenously.

This quantitative analysis of microcirculation was also accompanied by an efficient lactic acid washing, which is the clinical expression of what was observed in the microcirculation.

Lactic acid levels of up to 10 dropped to 4 mmol/L in two hours, and a short time later the lactic acid level is in the range of normality. After 24 h, 48 h and 72 h, the animal was standing, eating, having bowel movements and good diuresis, with good oxygenation and ventilation, with lactic acid levels less than or equal to the baseline levels in all measurements and ions in range.

A negative control group with one of the crystalloids commonly used in practice, Plasmalyte®, a balanced isotonic solution, was added. The lactic acid level in the animal is taken to a level higher than 5 mmol/L, as established in the protocol, and Plasmalyte infusion (3:1 ratio) was then performed. The lactic acid level remained high during the 2 h of observation, and after 3 h it was still at 6 mmol/L.

This result shows a clear difference with respect to the solution of the present invention.

At the microcirculation level, there were areas with 17% PPV, which explains why lactic acid levels did not decrease as was observed with the solution of the present invention. After 24 h, the animal was standing, had little appetite and pronounced weakness. An expiratory stridor, breathing difficulties and abdominal retraction were all observed. The auscultation showed bilateral hypophonesis. The arterial blood gas showed that hemoglobin oxygen saturation was 89% and pO2 was 60 mmHg, with an oxygen flow of 5 liters. This all seemed to indicate that the animal was experiencing acute lung edema. After sacrificing the animal, samples of different organs were taken; a loop edema was observed at the intestinal level, while this was not the case in the group of the solution of the present invention and in the whole blood group. The superiority of the solution of the present invention with respect to the Plasmalyte® is obvious. 24 h after, lactic acid level remained above baseline lactic acid level, which is a clear indicator that the microcirculation was not restored.

The solution of the present invention was compared with whole blood transfusion (less than 20 days of storage at 5° C.) applying a 1:1 ratio for resuscitation, which would be the ideal treatment in cases of hemorrhagic shock. The results were similar in reference to the analysis of microcirculation and lactic acid washing. During hemorrhagic shock, PPV dropped and after resuscitation with blood a PPV of 100% was reached, while this was not the case in all the measured areas, as in some there was still a PPV of 50% after one hour, while this was normal after 2 h. The lactic acid level exceeded 5 mmol/L and also returned to normality in over two hours. The animal had good aspect after 24 h, oxygenation and ventilation were adequate, the animal was eating, having bowel movements, urinating and had a good breathing dynamic.

The fact that the new crystalloid is not inferior with respect to whole blood in relation to microcirculation stands out. The results were not merely isolated cases, but rather were repeated successively in each and every one of the animals included in the test.

Table 3 shows the results in an animal treated with the solution of the invention. The animal weighed 32 kg and had an estimated blood volume of 2,200 mL. 40% of the blood volume was drawn, exceeding the lactic acid threshold of 5 mmol/L.

|  | Baseline | 25% drawn | 40% drawn | Shock | T0 | T15 | T30 FiO$_2$ 0.6 | T1h FiO$_2$ 0.8 | T1h FiO$_2$ 1 |
|---|---|---|---|---|---|---|---|---|---|
| MBP | 72 | 52 | 34 | 33 | 59 | 55 | 50 | 55 | 50 |
| HR/rhythm | 83 SR | 172 SR | 194 | 220 | 147 | 142 | 150 | 140 | 150 |
| SpO$_2$ | 100 | 100 | 100 | Not detected | 100 | 100 | 100 | 100 | 100 |
| EtCO$_2$ | 33 | 30 | 26 | 24 | 35 | 35 | 33 | 32 | 30 |
| FiO$_2$/PEEP | 0.4/5 | 0.4/5 | 0.4/5 | 0.4/5 | 0.4/5 | 0.4/5 | 0.6/5 | 0.8/5 | 1/5 |
| pH | 7.49 | 7.37 | 7.28 | 7.179 | 7.23 | 7.29 | 7.35 | 7.34 | 7.38 |
| EB | 3 | 3.1 | −1.2 | −11.4 | −8.7 | −7.9 | −5.5 | −3.7 | −4.8 |
| HCO$_3$ | 26.3 | 26.2 | 21.6 | 16.4 | 18.4 | 19 | 17 | 21.5 | 20.6 |
| pCO$_2$ A/V | 33.4/39.8 |  | /54 | 23.8/ | 40.6/47.9 | 38/46.9 | 35.4/43.9 | 36/42.7 | 34.1/43.7 |
| pO$_2$ | 191 |  |  | 206 | 215 | 360 | 368 | 520 | 550 |
| Na/K | 137/4 | 135/4.7 | 131/5.6 | 129/5.5 | 134/4 | 133/4.3 | 133/4.4 | 136/4.4 | 133/5.1 |
| Ca$^{2+}$/Cl | 1.36 | 1.39/99 | 1.38/95 | 1.31/100 | 1.63/112 | 1.60/112 | 1.54/112 | 1.55/113 | 1.50/111 |
| Hb/Hct | 9.5 | 11.9 | 12.4 | 12.2 | 5.7 | 5.8 | 5.3 | 4.4 | 5.8 |
| Lac | 2.5 | 2.9 | 5.7 | 6.6 | 4.1 | 3.5 | 3.1 | 2.4 | 1.5 |
| SatcvO$_2$ OER | 79.5 | 64.5 | 12.2 | 12% | 67.7 | 66.6% | 74.8% | 80.6% | 53.6% |
| CVP | 5 | 3 | 4 | 4 | 7 | 5 | 6 | 6 | 6 |
| MetHb | 1.6% | 1.7% | 3.4% | 1.3% | 2.4% | 2.9 | 2.5% |  | 1% |
| CI | 9.1 | 3.5 | 3.5 | 3 | 8 | 8.7 | 6.5 | 7.6 | 4.5 |
| SVV % | 11% | 18% | 26% | 24% | 27% | 24% | 26% | 24 | 24% |
| SVRi | 554 | 1262 | 727 | 784 | 473 | 442 | 553 | 456 | 704 |
| SVi | 108 | 20 | 18 | 19 | 55 | 55 | 43 | 53 | 30 |
| T | 35.4 | 35.4 | 35.2 | 35.1 | 35 | 35 | 35 | 34.7 | 34.5 |
| Intestinal PPV (%) | 100 | 100 | 100 | 70 | 100 | 100 | 100 | 100 | 100 |
| Brain/skeletal muscle rSO$_2$ | 56/54 | 56/50 | 54/47 | 51/38 | 59/55 | 59/56 | 59/56 | 61/58 | 60/56 |
| Diuresis |  |  |  |  |  |  |  |  | 300 cc |

MBP: mean blood pressure
HR: heart rate
SpO$_2$: peripheral oxygen saturation
EtCO$_2$: end-tidal CO$_2$
FiO$_2$: fraction of inspired oxygen
PEEP: positive end-expiratory pressure
EB: base excess
Hb: hemoglobin
Hct: hematocrit
SatcvO$_2$: central venous oxygen saturation
CVP: central venous pressure
MetHb: methemoglobin
CI: cardiac index
SVV %: stroke volume variation expressed as %
SVRi: systemic vascular resistance index
SVi: stroke volume index
PPV: proportion of perfused small vessels expressed as a %
rSO$_2$: regional tissue oxygen saturation. The first number refers cerebral saturation and the second one to muscular saturation.
Diuresis: amount of urine expelled by the animal at the end of the procedure.
SR: sinusal rhythm The solubility coefficient of oxygen in the solution of the invention at 36° C. was measured, and the coefficient is 0.006 mgO$_2$/mm Hg/dl. When comparing it with the solubility coefficient of oxygen in Plasmalyte®, which is 0.0041 mgO$_2$/mm Hg/dl and with the solubility coefficient of oxygen in blood plasma (not diluted), which is 0.0031 mgO$_2$/mm Hg/dl, all of which were measured at 36° C., the solubility coefficient of the solution of the invention was found to be superior to the others.

This is advantageous because it demonstrates the higher capacity of this new solution to dissolve oxygen. Oxygen dissolved in blood plasma is the oxygen not linked to hemoglobin and is very important in cases of critical anemia (Hb less than 3-4 g/dl).

Table 4 shows the results in an animal treated with Plasmalyte®. The animal weighed 21 kg, with an estimated 55% blood volume drained, exceeding the lactic acid threshold of 5 mmol/L stipulated in the protocol.

|  | Baseline | 25% drawn | 55% drawn | Shock | T0 | T15 | T30 FiO$_2$ 0.6 | T1h FiO$_2$ 0.8 | T1h FiO$_2$ 1 |
|---|---|---|---|---|---|---|---|---|---|
| MBP | 62 | 32 | 33 | 34 | 51 | 43 | 46 | 47 | 48 |
| HR/rhythm | 98 Sr | 179 SR | 202 sr | 200 sr | 172 sr | 184 | 192 | 202 | 197 |
| SpO$_2$ | 100 | 100 | No | No | 100 | 100 | 100 | 100 | 100 |
| EtCO$_2$ | 34 | 31 | 26 | 23 | 46 | 40 | 39 | 39 | 40 |
| FiO$_2$/PEEP | 0.4/5 | 0.4/5 | 0.4/5 | 0.4/5 | 0.4/5 | 0.4/5 | 0.6/5 | 0.8/5 | 1/5 |
| pH | 7.56 | 7.56 | 7.499 | 7.46 | 7.6 | 7.35 | 7.33 | 7.36 | 7.39 |
| EB | 8.7 | 6.3 | −0.8 | −4.7 | 0.7 | −0.1 | −0.4 | −0.1 | 1.9 |
| HCO$_3$ | 31.8 | 29.8 | 24 | 21.1 | 26.2 | 24.4 | 24.2 | 23.4 | 25.9 |
| pCO$_2$ A/V | 33.9/43.5 | 31.1/45.6 | 28.8/46.3 | 26.6/54.2 | 22.4/57.2 | 45/54 | 47.8/54.2 | 43.6/55.2 | 43.7/54.5 |

-continued

|  | Baseline | 25% drawn | 55% drawn | Shock | T0 | T15 | T30 FiO$_2$ 0.6 | T1h FiO$_2$ 0.8 | T1h FiO$_2$ 1 |
|---|---|---|---|---|---|---|---|---|---|
| pO$_2$ | 204 | 199 | 174 | 149 | 150 | 161 | 237 | 328 | 462 |
| Na/K | 138/4.1 | 137/5.1 | 135/6.9 | 135/7.6 | 140/4 | 140/3.4 | 141/3.9 | 140/3.7 | 139/4.1 |
| Ca$^{2+}$/CI | 1.34/100 | 1.38/101 | 1.33/102 | 1.33/102 | 0.84/99 | 1.14/99 | 1.16/99 | 1.19/100 | 1.28/99 |
| Hb/Hct | 9.5/29 | 10.8/33.1 | 12.4 | 12.7/38.8 | 4.9/14.9 | 8.8/27 | 8.5/26.1 | 8.3/25.4 | 8.5/26.2 |
| Lac | 1 | 1.7 | 5 | 7.3 | 5.9 | 6.7 | 7.6 | 7.4 | 5.8 |
| SatcvO$_2$ OER | 54.6 | 45.2 | 15.4 | 13 | 63.7 | 51.7 | 52.9 | 58.7 | 60.7 |
| CVP | 5 | 5 | 4 | 7 | 6 | 6 | 5 | 4 | 6 |
| MetHb | 1.9% | 1.6 | −0.9 | 0.9 | −0.4 | 1.1% | 0.5 |  | 3.3 |
| CI | 10.2 | 2 |  |  | 15.2 | 8.4 | 9.2 | 7.9 | 3.7 |
| SVV % | 18 | 26 | 32 |  | 25 | 31 | 26 | 31 | 30 |
| SVRi | 449 | 1225 |  |  | 171 | 370 | 369 | 438 | 387 |
| SVi | 101 | 11 | 29 |  | 81 | 43 | 47 | 41 | 30 |
| T | 35.2 | 35.6 | 35.9 |  | 35.5 | 35.6 | 35.8 | 35.9 | 36.2 |
| Intestinal PPV (%) | 100 | 100 | 95 | 95 | 62 | 87 | 100 | 72 | 97 |
| Brain/skeletal muscle rSO$_2$ | 50/61 | 48/57 | 47/42 | 48/39 | 53/54 | 55/61 | 54/62 | 56/58 | 46/53 |
| Diuresis |  |  |  |  |  |  |  |  | 300 cc |

Table 5 shows the results in an animal treated with whole blood, with 60% blood volume drained, exceeding the lactic acid threshold of 5 mmol/L.

|  | Baseline | 25% drawn | 60% drawn | T0 | T15 | T30 FiO$_2$ 0.6 | T1h FiO$_2$ 0.8 | T2h FiO$_2$ 1 |
|---|---|---|---|---|---|---|---|---|
| MBP | 75 | 50 | 35 | 62 | 60 | 80 | 73 | 84 |
| HR/rhythm | 100 SR | 163 | More than 200 | 156 | 176 | 169 | 119 | 87 |
| SpO$_2$ | 100 | 100 | Not detected | 100 | 100 | 100 | 100 | 100 |
| EtCO$_2$ | 31 | 32 | 33 | 43 | 41 | 39 | 35 | 34 |
| FiO$_2$/PEEP | 0.4/5 | 0.4/5 | 0.4/5 | 0.4/5 | 0.4/5 | 0.6/5 | 0.8/5 | 1/5 |
| pH | 7.48 | 7.515 | 7.46 | 7.329 | 7.4 | 7.41 | 7.49 | 7.53 |
| EB | 6.1 | 4.8 | −3 | −1.4 | 1.4 | 3.4 | 6.6 | 10.5 |
| HCO$_3$ | 29.5 | 28.3 | 22.4 | 23.2 | 25.6 | 26.7 | 29.9 | 33.9 |
| pCO$_2$ A/V | 38.8/45.4 | 34.3/44.3 | 28.5/47.8 | 46.6/56.7 | 41.4/63 | 43.5/49.7 | 38.7/47 | 38.8/43.7 |
| pO$_2$ | 233 | 217 | 150 | 197 | 194 | 280 | 331 | 317 |
| Na/K | 138/4.6 | 135/4.9 | 131/6 | 136/4.7 | 137/4.7 | 137/4.5 | 137/4.4 | 136/4.6 |
| Ca$^{2+}$/CI | 1.39/100 | 1.36/99 | 1.26/100 | 0.89/94 | 2.31/99 | 1.27/96 | 1.32/97 | 1.40/95 |
| Hb/Hct | 9.8/30 | 9.1/28 | 13/39.8 | 11.2 | 10.5 | 10.1 | 10.1 | 10.1 |
| Lac | 3.3 | 4.2 | 6.4 | 6.7 | 6.3 | 4.9 | 3.1 | 1.7 |
| SatcvO$_2$ OER | 71.7% | 49.5 | 33.7 | 77.3 |  | 89.5% | 88.2% | 79.2 |
| CVP | 7 | 4 | 3 | 4 | 6 | 7 | 6 | 7 |
| MetHb | 2% | 1.4% | 0.7% | 1.1% | 0.9% | 0.8% | 0.3% | 1.3% |
| CI | 7.3 | 3.8 | 3.7 | 13.3 | 16.2 | 11 | 10.7 | 8 |
| SVV % | 8% | 14% | 17% | 10% | 5% | 8% | 9% | 10% |
| SVRi | 896 | 1029 | 1106 | 371 | 325 | 376 | 454 | 659 |
| SVi | 73 | 21 | 19 | 82 | 119 | 68 | 88 | 85 |
| T | 36 | 35.6 |  | 36 | 35.8 | 35.6 | 35.8 | 35.6 |
| Intestinal PPV (%) | 100 | 100 | 92 | 67 | 79 | 95 | 100 | 100 |
| Brain/skeletal muscle rSO$_2$ | 70/60 | 80/54 | 66/44 | 60/64 | 65/67 | 65/69 | 64/70 | 58/64 |
| Diuresis |  |  |  |  |  |  |  | 90 cc |

The data shows that the solution of the invention yields better results than the Plasmalyte solution. This is evident as regards metabolic and hemodynamic management, as well as the management of the clinical status of the animals in the experiments. Compared with whole blood, it is clearly not inferior, placing it in a very advantageous position. It should be pointed out that the blood used for the experiments is whole blood with less than 20 days in storage. The blood that is transfused to patients is usually stored during up tp 42 days. This banked blood is referred to as "old blood" and its biochemical and structural state greatly differ from that of fresh blood. This may have clinical impact since "old" stored blood suffers biochemical changes (drop in ATP, drop in 2,3 DPG, etc.) and morphological changes (transformation of erythrocytes into echinocytes which are not adaptable to the microcirculation). Stored blood has a limited oxygen delivery capacity, and rather than restoring perfusion, it frequently impairs it.

A lactates chart as an outcome comparison at 24 h, 48 h and 72 h shows eloquent results. When comparing outcome lactates with baseline lactates, we see that the animals treated with the solution of the present invention had a lactate that was interior or the same as baseline lactate. This was not the case in Plasmalyte and Whole blood group. In Plasmalyte group many lactates at 24/48/72 h were superior to baseline Lactate and in Blood group some of lactates were superior to baseline lactate. Lactate is the best marker we have currently to test the microcirculation since it is a marker of tissue recovery (oxygen debt recovery) and is greatly related to survival rates after hemorrhagic shock.

Table 6 shows lactates comparison at 24 h, 48 h and 72 h

|  | Baseline Lac | Lac at 2 h after resuscitation | Lac 24 h | Lac 48 h | Lac 72 h |
|---|---|---|---|---|---|
| Ox2 | 3 | 4.4 | 1 | 0.7 | 3 |
| Ox4 | 2.5 | 1.5 | 1.9 | 1.2 | 1.7 |
| Ox6 dead | 2.3 | 4.3 |  |  |  |
| Ox7 | 2.7 | 1.4 | 1.7 | 2.1 | 1 |
| Ox8 | 1.5 | 1.8 | 0.6 | 0.9 | 0.8 |
| Ox10 | 1.5 | 1.9 | 1.2 | 1.5 | 1.6 |
| S1 dead | 2 | 2.4 |  |  |  |
| S2 | 3.3 | 1.7 | 1.3 | 1.5 | 4.9 |
| S3 | 2.3 | 2 | 1 | 2.3 | 0.3 |
| S4 | 1.4 | 5.1 | 1.4 | 1.3 | 1 |
| S5 | 3.8 | 2 | 1.9 | 8.5 | 3.5 |
| S6 | 1.8 | 1.9 | 0.8 | 1.5 | 3.4 |
| P1 | 0.8 | 1.3 | 2.5 | 1.3 | 1.5 |
| P2 | 1 | 5.8 | 1.9 | 0.8 | 0.6 |
| P4 | 1.6 | 1.4 | 2.8 | 4.4 | 1.1 |
| P5 | 1.1 | 2.3 | 2.3 | 1.9 | 1.3 |
| P6 | 2.7 | 2.5 | 2.3 | 3.6 | 3.1 |
| P7 | 2.2 | 1.5 | 0.7 | 4.2 | 1.5 |

Ox stands for the solution of the present invention.
S stands for Whole Blood group
P stands for Plasmalyte group
Animals are numbered
Lac refers to Lactate levels expressed in mmol/L It should be pointed out that in the group of animals treated with the solution of the present invention, a higher consumption of bases (bicarbonate) was observed when compared with whole blood and Plasmalyte groups. This could be related to the recruitment of capillaries that collapsed during hemorrhagic shock and the release into systemic circulation (macrocirculation) of acid metabolites resulting from tissue hypoxia. The highest consumption of bases in the group of animals treated with the solution of the present invention is correlated with optimal lactic values at 24/48/72 hours, therefore, the solution of the present invention improves metabolic management in bleeding patients since the microcirculation is "cleaned" from acid metabolites. All this would, again, improve survival rates in hemorrhagic shock.

After administering a dose of lethal potassium chloride under sedation to each animal, a comparative histological analysis of the three groups was performed. The atrium, ventricle, aorta, vena cava, lung, liver, spleen, intestine, mesenteric lymphatic node and kidney were analyzed. In the group of animals treated with the present invention, no signs of toxicity or any chemical element deposit were observed in any of the tissues analyzed.

The invention claimed is:

1. An isotonic crystalloid aqueous solution, comprising $Na^+$ ions in a range comprised between 50 and 200 mmol/L, $K^+$ ions in a range comprised between 1 and 10 mmol/L, $Cl^-$ ions in a range comprised between 50 and 200 mmol/L, characterized in that it has nitrate ions or nitrite ions or mixtures thereof in a range comprised between 0.0001 mmol/L and 1 mmol/L, $Mg^{2+}$ ions in a range comprised between 5 and 20 mmol/L, $HCO_3^-$ in a range comprised between 0.1 mmol/L and 2 mmol/L, $SO_4^{2-}$ in a range comprised between 4 mmol/L and 8 mmol/L, and at least a chemistry element selected from: Li, Be, B, Al, Si, P, Sc, V, Cr, Mn, Fe, Co, Ni, Cu, Zn, As, Br, Rb, Sr, Y, Zr, Mo, Pd, Ag, Sn, Sb, I, Cs, Ba, Ce, Ho, Au, Tl, Pb, Bi, Th and U, wherein the solution has a solubility coefficient of 0.006 mg $O_2$/mmHg $pO_2$/dL at 36° C.

2. The isotonic crystalloid aqueous solution according to claim 1, further comprising $Ca^{2+}$ ions in a range comprised between 1 and 20 mmol/L.

3. The isotonic crystalloid aqueous solution according to claim 1, further comprising $Ca^{2+}$ ions in a range comprised between 1 and 10 mmol/L.

4. The isotonic crystalloid aqueous solution according to claim 3, wherein the range of nitrate ions or nitrite ions or mixtures thereof is comprised between 0.0001 mmol/L and 0.06 mmol/L.

5. The isotonic crystalloid aqueous solution according to claim 1, wherein the range of nitrate ions or nitrite ions or mixtures thereof is comprised between 0.0001 mmol/L and 0.06 mmol/L.

6. The isotonic crystalloid aqueous solution according to claim 1, comprising the following chemistry elements: Li, Be, B, Al, Si, P, Sc, V, Cr, Mn, Fe, Co, Ni, Cu, Zn, As, Br, Rb, Sr, Y, Zr, Mo, Pd, Ag, Sn, Sb, I, Cs, Ba, Ce, Ho, Au, Tl, Pb, Bi, Th and U.

7. The isotonic crystalloid aqueous solution according to claim 1, for use as a drug.

8. The isotonic crystalloid aqueous solution according to claim 1, for use as a vasodilator.

9. The isotonic crystalloid aqueous solution according to claim 1, for use in the treatment of hemorrhagic shock or in acute normovolemic hemodilution.

10. The isotonic crystalloid aqueous solution according to claim 1, for use as an intravenous fluid replacement.

11. The isotonic crystalloid aqueous solution according to claim 1, for use in the prevention of ischemia-reperfusion injury.

12. The isotonic crystalloid aqueous solution according to claim 5, for use as a drug.

13. The isotonic crystalloid aqueous solution according to claim 5, for use as a vasodilator.

14. The isotonic crystalloid aqueous solution according to claim 5, for use in the treatment of hemorrhagic shock or in acute normovolemic hemodilution.

15. The isotonic crystalloid aqueous solution according to claim 5, for use as an intravenous fluid replacement.

* * * * *